United States Patent
Pang et al.

(10) Patent No.: US 6,840,933 B1
(45) Date of Patent: Jan. 11, 2005

(54) METHOD AND APPARATUS FOR TREATING NEOVASCULARIZATION

(75) Inventors: Kian Tiong Pang, Jurong (SG); Joshua Ben-Nun, Moshav Beit-Herut (IL)

(73) Assignee: Cantos United Corp., Ubanizacion Obarrio (PA)

( * ) Notice: Subject to any disclaimer, the term of this patent is extended or adjusted under 35 U.S.C. 154(b) by 0 days.

(21) Appl. No.: 09/913,528
(22) PCT Filed: Feb. 15, 2000
(86) PCT No.: PCT/IB00/00274
§ 371 (c)(1), (2), (4) Date: Dec. 13, 2001
(87) PCT Pub. No.: WO00/47107
PCT Pub. Date: Aug. 17, 2000

(30) Foreign Application Priority Data

Feb. 15, 1999 (GB) .............................. 9903394

(51) Int. Cl.[7] .............................................. A61B 18/20
(52) U.S. Cl. ................ 606/4; 606/10; 606/13; 600/479; 604/20
(58) Field of Search .................. 600/479; 606/4, 606/6, 10–13; 514/63; 604/20

(56) References Cited

U.S. PATENT DOCUMENTS 5,279,298 A    1/1994  Flower
5,935,942 A *  8/1999  Zeimer .................... 514/63

FOREIGN PATENT DOCUMENTS

WO   WO 96/18415   6/1996
WO   WO 98/46122   10/1998

OTHER PUBLICATIONS

"Laser–based fundus camera for infrared angiography," *Optical Engineering*, vol. 34 No. 3 pp. 737–745 (Mar. 1995).

* cited by examiner

Primary Examiner—David M. Shay
(74) Attorney, Agent, or Firm—Sterne, Kessler, Goldstein & Fox P.L.L.C.

(57) ABSTRACT

A method for detecting and treating diseases of a type associated with the growth of new blood vessels (neovascularization) in choroidal or subretinal layers of the eye and which can be used for more accurately locating a feeder vessel to the neovascularization and for blocking such a feeder vessel by photocoagulation with a laser.

Figure 1:
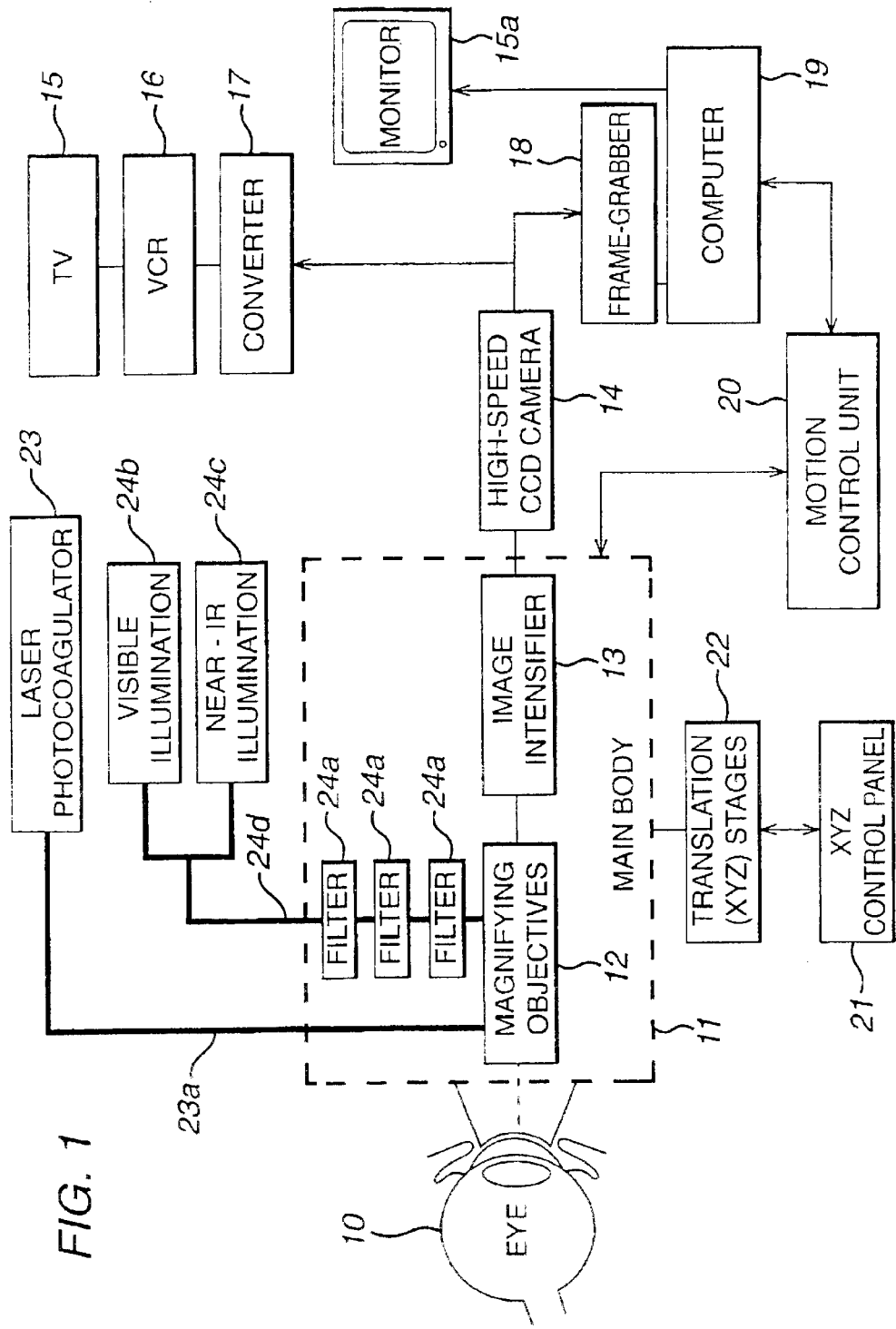

28 Claims, 4 Drawing Sheets a = ARTERIAL
v = VENOUS

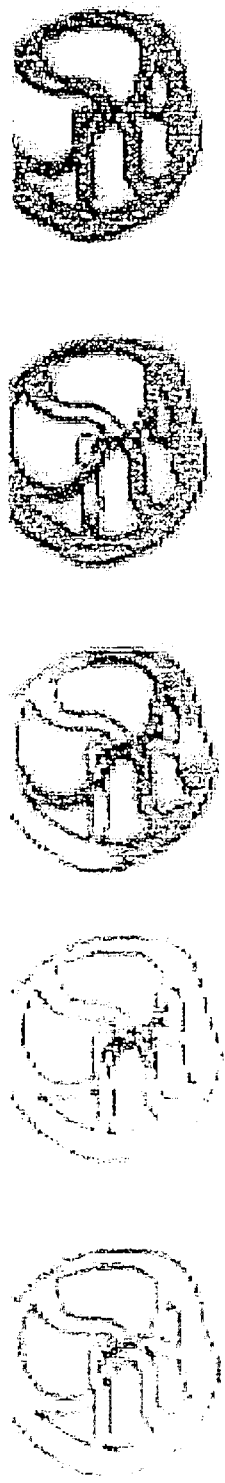
FIG. 5a  FIG. 5b  FIG. 5c  FIG. 5d  FIG. 5e

METHOD AND APPARATUS FOR TREATING NEOVASCULARIZATION

The present invention relates to a method and apparatus for detecting and treating diseases of a type associated with the growth of new blood vessels (neovascularization) in choroidal or subrecinal layers of the eye. More particularly, the invention can be used for more accurately locating a feeder vessel to the neovascularization and for blocking such a feeder vessel by photocoagulation with a laser.

Age-related Macular Degeneration (AMD) is a chronic disease affecting primarily the choriocapillaris, Bruch's membrane and the Retinal Pigment Epithelium (RPE). It is the most common cause of legal, irreversible blindness in patients aged 65 and over in the US, Canada, England, Wales, Scotland and Australia. Although the average age of patients when they lose central vision in their first eye is 65 years, some patients develop evidence of the disease in their fourth or fifth decade of life.

Approximately 10% to 15% of patients manifest the exudative form of the disease. Exudative AMD accounted for 79% of legally blind eyes. The disease is bilateral with accumulating chances of approximately 10% to 15% per annum of developing the blinding disorder in the fellow eye. The recurrence rate of a treated neo-vascular membrane has been estimated to be 50% within 18 months, but more recent research with Photo-Dynamic Therapy (PDT) has indicated a recurrence rate of 50% within 12 weeks from the last treatment.

The hallmark of the exudative form of the disease is a Choroidal Neo-Vascular Membrane (CNVM) that grows beneath the retina or the RPE in the foveal-macular region. This CNVM leaks and bleeds evoking a scaring reaction that eventually results in the scaring of the affected area with consequential blindness. Histopathology of these CNVMs revealed that the vast majority of the membranes are nourished by a few (1 to 3) feeder vessels only. This means that only a few "vascular bridges" connect the origin of the CNVM (in the choroid) to the new location beneath the retina or the RPE.

The currently available treatment, as recommended by the Macular Photocoagulation Study (MPS) is massive destruction of the membrane with an appropriate laser. Unfortunately, most of the membranes are sub-foveal when discovered and such a treatment modality leads to the complete destruction of all tissues—CNVM and retinal—within the treated area. It has been suggested that focusing on feeder vessel destruction will minimise the collateral damage caused by massive tissue ablation. The major problem with this feeder treatment is the limited patient eligibility because of the difficulty in identifying feeder vessels. (Ref: F Shiraga, et al. OPHTHALMOLOGY, 105#4, 662–669, April 1998.)

Thus existing techniques for the treatment of AMD can not treat the disease satisfactorily. The known techniques routinely damage blood vessels and tissues unrelated to the disease or the disease-causing areas. Essentially, these techniques lack the ability to locate and destroy feeder vessels to the neovascularization with sufficient accuracy.

One object of the present invention to provide a method of treatment of neovascularization that overcomes or at least ameliorates the disadvantages identified.

Another object of the present invention to provide apparatus which can be used for more accurate determination of the location of feeder vessels to the neovascularization.

Accordingly, a first aspect of the invention provides a method of treating neovascularization in the eye of patient comprising:

(i) introducing a detectable marker into the circulation of the patient at a point remote from the eye;
(ii) observing a region of suspected neovascularization in the eye after introducing the marker;
(iii) detecting the location of the onset of the marker into the region in order to determine the location of a feeder vessel to the region of neovascularization or an anomaly in the retinal pigment epithelium; and
(iv) photocoagulating the feeder vessel to prevent it from feeding blood to the neovascularization.

The invention also provides apparatus for examination of neovascularization in an eye of a patient, comprising:

a light source for exciting a dye introduced into the circulation of the patient;
an image generator for generating an image of a region of the eye under examination; and
an image recorder for recording a plurality of images of the region.

WO-A-98/46122 describes one form of apparatus which, together with the modifications and/or improvements described herein, can be used in preferred embodiments of the invention. Where applicable, the contents of WO-A-98/46122 are incorporated herein by reference.

Typically, the detectable marker is a fluorescent dye, the region is illuminated by radiation that excites the dye and the first appearance of the dye in the region is detected as an increase in brightness by a predetermined amount above background levels. In an example of the invention in use, a video image of the region is monitored for the first appearance of the dye. Initially, the image is dark, indicating that no fluorescent dye has entered a blood vessel contributing to the image. As soon as the dye does enter the field of the image, it is visible as an area of increased brightness and its position and course is readily seen and recorded.

As the time between the first appearance of the marker with just one or a small number of areas of brightness in the image and the filling of most of the image with the dye is usually very short, of the order of fractions of a second, it is preferred that the region is observed by recording a succession of images of the region using an image recorder and subsequently examining the recorded images to identify the location of a blood vessel feeding blood into the region. This enables images to be stored for later examination. A suitable rate of capture of images is at least 30 per second, though it is preferred that the rate is at least 45 per second, and higher rates such as 60 per second and greater will tend to give improved identification of feeder blood vessel location.

In an embodiment of the invention, the recording of images of the region is triggered by triggering means associated with the image recorder and sensitive to an increase of the marker in the region. The trigger can be set so as to trigger image capture when the brightness level rises above the average background level plus a predetermined amount. This may be initially set at a level of, say, 10 percent but is usually optimised empirically. Computer memory usage for image storage is relatively high, and thus this embodiment is of benefit in that unnecessary storage of image prior to the first appearance of the dye in the region is reduced and may even be totally avoided.

In an alternative embodiment of the invention, the recording of images of the region is immediately initiated at the injection of the marker(s). In this embodiment, the total recording time must be of ample length so as to record the earliest appearance of the marker in the region (and even into later periods when the marker accumulates and fills in the region). The total recording time should preferably be 30 seconds or more for storing images at a rate of 30 full frames per second, minimum. It is even more preferable to have a total recording time of 30 seconds or more for storing images at a rate of 60 full frames per second or more. In this embodiment, no triggering or empirically determined threshold is required as ample recording media (memory) is provided to store the entire captured sequence of images. Thus, no particular sensitiveness to the increase of the marker is required.

In a further embodiment of the invention, the method additionally comprises introducing a second detectable marker into the circulation of the patient, and detecting the location of the second detectable marker in the region so as to determine the position of the blood vessel walls in the region. This second marker is generally used to identify blood vessels throughout the region, so as to build up a map or network of the vasculature especially the blood vessel walls of the feeder vessels suspected of causing or contributing to the disease. This second detectable marker can be used in real time, not needing the fast image capture of the first marker. In use, the image or images showing the location of the first appearance of the first detectable marker into the region are compared with the position of the blood vessel walls located by the second detectable marker, such as by overlaying one image onto the other, so that it is possible to determine the location of a blood vessel feeding blood into the region. This introduces further accuracy into the identification of the feeders, or, a confirmation of the locations of suspected feeder blood vessels. For example, if the CNVM is under examination, the stained blood vessel walls can be compared with the positions of the first fillings of the region and only those overlapping areas are to be considered as feeder vessels to be treated.

The treatment to be applied may be by conventional laser photocoagulation. In addition, it is a preferred embodiment of the invention that the treatment is carried out using a laser having the same absorption wave band of the second detectable marker.

In apparatus embodying the invention, an image generator generates an image of a region of the eye under examination; and an image recorder records a plurality of image frames of the region. The image recorder preferably records images at a rate of at least 30 frames per second, or faster, and for a total recording time of not less that 30 seconds (at whichever rate being used).

In a preferred embodiment of the invention, the apparatus the further comprises a trigger means associated with the image recorder and sensitive to an increase of the marker in the region, wherein it triggers image recording in response to an increase of the marker in the region above a predetermined level.

Thus using the method of the invention, in order to locate a target, it is not necessary to see the target clearly or sharply, as long as the target is marked or contrasted or is easily differentiated from the background by a visible marker, e.g. a dye.

Embodiments of the invention will now be described with reference to the accompanying drawings in which:

FIG. 1 is a schematic diagram of opthalmalogical apparatus for examining and treating the eye.

Figure 2:
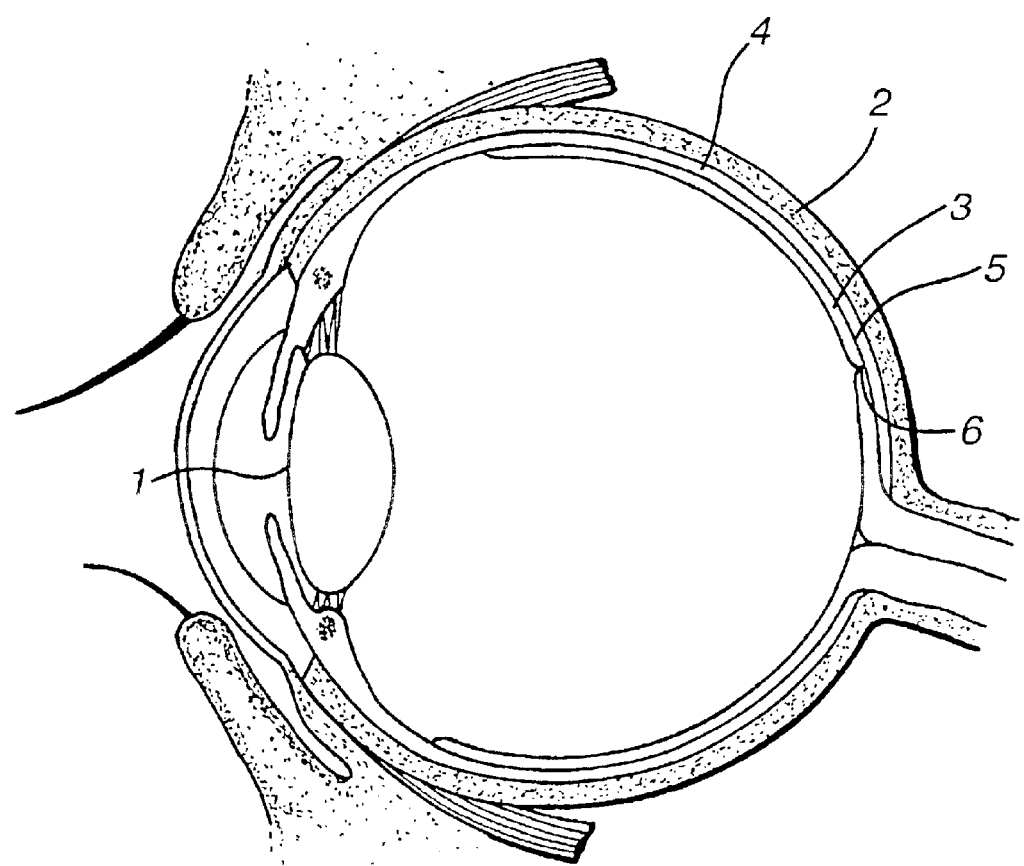
Figure 3A:
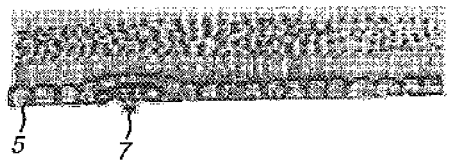
Figure 3B:
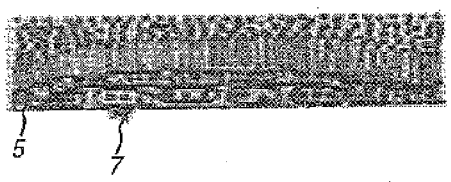
Figure 3C:
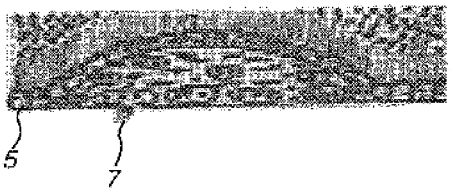
Figure 4A:
Figure 4B:
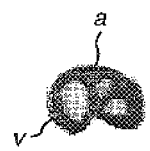
Figure 4C:
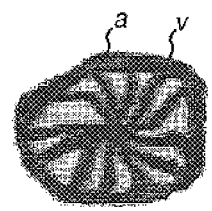

FIGS. 2 and 3 schematically illustrate parts of the eye.

FIGS. 4*a*-4*c* and 5*a*-5*e* show image frame sequences and the spread of a marker into a feeder region of a neovascularization.

Referring first to FIG. 2, this shows schematically a section through the eye and illustrates the lens 1 of the pupil region, the schlera 2, and retina 3. The section also shows the choroid 4, pigment epithelium 5 and fovea 6. Referring next to FIGS. 3*a*-3*b*, these schematically illustrate a magnified portion of the eye including the RPE (retinal pigment epithelium) 5, shown as a layer. FIGS. 3*a*-3*b* are shown as a sequence to illustrate the anatomy and growth of the CNVM (choroidal neo-vascular membrane). This includes the RPE, which is furthest from the cornea, protruding feeders and the CNVM itself which grows into the retina or pushes the RPE upwards causing a "bump" in the retina (as depicted by the sequence of FIGS. 3*a*-3*b*). The invention enables the location of a feeder 7 to the neovascularization to be more accurately determined (compared with the techniques described in WO-A-98/46122). For example, after introducing a marker into the patient's circulatory system, the marker can be detected in the foveal-macular region of the patient's eye when it starts to fill the feeder, whereby the location of the feeder 7 to the neovascularization can be accurately determined so that a laser can be subsequently used to cause photocoagulation, thereby blocking the feeder. In carrying out this method, a high speed CCD camera is coupled to an image intensifier which in turn is coupled to the optical system that is focused on a region where a feeder 7 is suspected. Whilst this does not essentially require confocal paths, they would be useful for focusing on a thin slice. For example, if such a slice were thinner than the gap between the choroid or RPE and the CNVM, the optical system can be focused on feeders suspected to be located somewhere between the top and bottom of the "bump", while the RPE and CNVM would remain out of focus, i.e. blurred out. However, the confocal system is not essential in every case. The choroid cannot be seen because it is shielded by the RPE (which is opaque to visible light) and to see the choroidal vasculature, ICG (in the IR) and the confocal capability to focus above the choriocapillaris can be employed to detect the lesion protruding into the RPE, the marker being a substance such as fluoroscein (in the visible blue/green). Whilst fluoroscein filling of the choroid is not visible (because of the RPE), unless there are breaks in the RPE (due to the feeders/CNVM of a disease, or just "window defects", feeder filling will be seen followed by the neovascular network filling, by observing bright spots against a dark RPE background. i.e. with focus on or about the RPE/retina. This is schematically illustrated by the sequence FIGS. 4*a*-4*c*, which show respectively the start of the filling of the feeder and the subsequent filling of vessels by capturing frames of image information with the high speed camera. Almost immediately after the appearance of bright spots indicating the locations of feeders, the visible retinal vascularture fills, producing a brilliant flash which drowns out all the spots. By careful selection and adjustment of timing, i.e. to ensure that sufficient image frames are captured at a high enough frame speed, the captured frames show the first appearance and subsequent growth of these spots. These frames (of interest) which are taken over a very short period of time, can be subsequently examined and analysed to see how the brightness of each spot develops (between the choroidal filling and the retinal flash). Confocal paths are of use because they enable narrow focusing on a layer just above the RPE and not too much into the retina. In this way, the retinal flash can be reduced or eliminated (i.e. noise reduction/elimination. Then ICG and the confocal system (if needed) can be used to confirm that these spots are diseased (and not window defects in the RPE). Disease spots are stained by ICG in the longer term (e.g. of 3–5 minutes post-injection). By then superimposing flouroscein stills on the live, evolving ICG staining, and focusing on the thin layer about the spot (so as not to excite the ICG, which may still be coursing through the normal choroidal and retinal vasculature—but which would be out of focus in the confocal system), the disease spots can be confirmed, targeted and treated.

Fast cameras and fast computers can be used to catch those images between the invisible filling of the choroid and the invisible filling of the retinal vessels. There is no need for specific focusing at locations where feeders are suspected to exist. It would help in signal discrimination, especially with confocal paths, but is not necessary if frames can be captured in the intervening few milliseconds between sequential fillings. Hence, one would see dark, a few brightening spots and then the flash of the retinal vessels. Referring to FIG. 1, this schematically illustrates the kind of apparatus which can be used to carry out the invention. Reference is also made to WO-A-98/46122, for further details of the optical and other systems which are represented schematically in FIG. 1 by the main body 11, which includes inter alia the magnifying objectives 12. FIG. 1 shows the eye 10 positioned in front of the lens system and further details of this will be apparent from WO98/46122. Arranged on the image path is an image intensifier 13 coupled to high speed CCD camera 14. This is linked to video image generating apparatus including a TV unit 15, CCR 16 and image converter 17. Monitor 15a enables images to be viewed. Camera 14 also has a input for a frame grabber 18 which is linked to computer 19. Motion control unit 20 is coupled between the main body 11 and computer 19. An XYZ control panel 21 is coupled to translation (XYZ) stages 22 also coupled to the main body 11. A laser photocoagulator 23 is connected by means of a fibre optic light guide to the magnifying objective lens system 12. A visible illumination source 24b and a near IR illumination source 24c are on an illumination path 24d to a filter system 24a which is coupled to the magnifying objectives 12.

Essentially, the system disclosed in WO-A-98/46122 is upgraded with more speed, more RAM, and image capturing means which enable images to be captured in the required brief time interval and with the necessary spatial resolution, so that the feeders can be identified and treated. The distribution of the marker inside the target region, such as within a CNVM, always starts at the feeder or feeders. Consequently, the more closely temporally-spaced images are captured during the first second of the marker's entry into the CNVM, the better the chances of locating and confirming the feeders. That is, each image should be captured in as short a period as possible (i.e. high temporal resolution), and, the time elapsed between consecutively captured images should be as short as possible (i.e. high rate of capture). In addition, each image should have as high an image resolution as achievable so that details of the region can be seen. The invention may use any high speed image—capturing devices or sensors currently available to achieve improved identification of the feeder vessels.

Where triggering and threshold detection are not required, a feeder can be identified and located by the following technique.

(i) The entire captured sequence can be replayed in "slow-motion-stop-frame" so that the few (consecutive) images in which the marker first appears can be identified.

(ii) The brightening regions (or spots) in one of these images can be defined (marked out) and "registered".

(iii) A graph plotting the brightness levels (within each of the registered spots in every image in the captured sequence) against the order of the images (in the captured sequence).

(iv) In this manner, the brightness changes (increases) with time, within each registered spot, from before the marker arrives to well after the marker has filled the spots, can be illustrated graphically. Any suitable type of graphs can be used: 2-dimensional, 3-dimensional, histogram, etc.

(v) The rise and fall of the graph of each registered spot identifies a spot as a suspected feeder, or a "window defect" in the RPE. A feeder will fill with the marker and maintain its saturated brightness. A break (in the RPE) will show the underlying flash followed by a reduction in the brightness over several seconds (hundreds of images) before the brightness level rises again in the redistribution of the bolus. Hence, feeder locations are identified.

(vi) Other anomalies (in the RPE) can be studied by this method.

It has been found that magnification is more important than resolution when searching for a feeder vessel. In preferred embodiments of the invention, an operator may trade off a decision not to pursue higher resolution to enable a better view of a feeder. Preferably, accurate destruction of the feeders should be performed immediately once they are identified, and the invention advantageously provides for these functions both to be incorporated in one instrument.

In a specific embodiment of the invention, two fluorescent dyes, ICG and fluorescein, are injected into the circulation (simultaneously or separately) as is done in any current angiographic imaging procedure. At the earliest entrance of the fluorescein into the choroidal circulation, the increase in the brightness of the background haze is detected by the instrument, which then automatically self-triggers the image acquisition. The very earliest filling of the CNVM is acquired as rapidly as possible using a (digital) camera operating at a rate of 60 frames per second. The faster the image acquisition, the better the details of the earliest appearance of the dye, the better the ability to locate and confirm feeder vessels. All the images acquired during this early phase are presented on the computer monitor to be studied by the instrument operator(s). The earliest images that show the entry of the fluorescein into the CNVM are isolated and selectively stored as individual flames (marked or numbered or both) in the computer memory.

Image processing (software) is then used to analyse and enhance the location(s) where the fluorescein starts its entry into the CNVM. While executing this procedure of analysing fluorescein early filling, the second marker, ICG, is staining the vessel walls of the CNVM. This staining process is being monitored, in real time, by the instrument operator(s). The stored image(s) of the first (fluorescein) marker's early filling is recalled, made semi-transparent and then overlaid or otherwise superimposed on the real-time image of the ongoing staining of the membrane by the second marker. Only the stained vessels of the CNVM that are within the marked areas of the stored early (fluorescein) filling images are to be considered as possible feeders. A (100(m laser spot of appropriate power is aimed directly at the suspected feeder(s) and the treatment mode (photocoagulation) is executed. Preferably, the laser spot size should be between (50(m and (100(m to adjust to the expected cross-sections of the feeder vessels. Even more preferably, the laser spot size itself may be adjusted, in real time, by any combinations of optical and opto-mechanical means, between these limits. An aiming beam enables accurate laser shots to be applied to the target(s).

The wavebands of the treatment laser used for the treatment and the aiming are the same as that needed to excite the fluorescent marker (ICG) that stains the vessel walls of the CNVM. In this way, it is possible to combine better targeting and better treatment at lower powers due to enhancement in the absorption (of laser energy) by the second marker.

The instrument itself may also include a self-tracking system that uses the large vessels at the rim of the optic disc as alignment reference points in order to overcome the patient's unintentional eye movements.

The method of the invention is found to produce good results as it enables high magnification of the CNVM (while compromising on resolution). This "trade-off" is possible in the embodiments of the invention because the targets are marked with fluorescent markers.

The overlaying of the locations of early filling obtained by the first marker on the real-time image showing the staining of the CNVM walls by the second marker enables identification and confirmation of the feeder vessels that contribute to the disease. These specific vessels may then be considered for laser photocoagulation treatment without the massive destruction of areas of healthy vasculature and tissue.

The use of a laser that emits in the same waveband as the excitation waveband of the marker that stains the vessel walls confers the further benefit of less collateral damage due to the lower laser power needed to block the stained vessels.

The "self-tracking" embodiments of the invention can be likened to computerised finger-print recognition, at a basic level. It may be achieved using the following steps. The computer remembers a "map" (image) with key (user-registered) landmarks. Upon receiving a new image (live or still), it uses that (stored) map, rotates it, scales it, or uses any (known) means to find out if the new image is the same as the map but in a different orientation and/or scale. The "self-tracking" function has 2 parts:

(i) once the first (map) image is registered (in the memory) with its landmarks (e.g. where major vessels emanate from the edge of the optic disc), the software must find the same location every time (and maybe, be able to move the machine to the re-oriented map position), and, (ii) if required to zoom in on a specific area within the new image (i.e. re-scale the new image), the software must triangulate (based on the landmarks) and memorise the co-ordinates so as to zoom in, (and maybe later, zoom out to the scale of previous image). It must also keep the machine pointed at the same spot during any operations.

Below are the descriptions of specific embodiments of the invention to illustrate the invention in a non-limiting way.

EXAMPLE 1

Using Threshold Triggering

A flow chart of a method of the invention is thus:
S1: Main Start
(
S2: Fluorescein Sequence
(
S3: ICG Sequence
(
S4: Treatment Sequence
(
S5: PDT Sequence In more detail, a method of the invention is carried out as follows.

MAIN START—S1

The patient is prepared:

Measure the curvature of the cornea for the best-fitting (or the closest-fitting) contact lens to use.

Dilate the pupil, insert the lid retractor, etc.

Adjust the fixation light, the head-chin rest and the seat height to pose the patient in an appropriate and comfortable.

Insert an intravenous tap (through which the dyes can be injected) usually at the back of one hand.

FLUORESCEIN SEQUENCE—After completing S1

Use "general illumination" (any colour) to aim at the appropriate area, adjusting the illumination intensity, the magnification and the focus (in any order) to achieve the required field of view and details. (Illumination is adjusted to the appropriate minimum levels such that clear, low-noise images can be seen, i.e. no exact magnitude can be stated as it depends on the optics and media of the machine and the human eye. The images are black and white, using grey level determination.)

Usually, use low magnification (and therefore wider field) to begin.

Once the general (or specific area) is in focus, change the filters to the appropriate set (blue excitation, (=480–495 nm; green barrier, (=515–535 nm) for fluorescein.

Prepare triggering software:

Preset to capture images at the maximum frame rate (60 full frames per second because of the blood flow rate—it takes 10–25s after injection for the dye to arrive in the eye) for the maximum length of time permissible. (The latter is limited by the size of the computer memory).

Take a background scan of the image using the chosen filter set. The image is black (if no fluorescein is present) as the barrier filter does not pass the blue excitation illumination.

Set the triggering threshold to be the background level plus xx units. (xx is empirically established or estimated. The units are usually grey levels. The threshold is usually the average brightness of the entire image or the diagonal strips of pixels across the image, etc—depending on the speed of the computer, the CPU time allowed for the averaging operations, etc. Or, any other sensitive measure of brightness changes in an image.) Hence, the threshold is relative to the "background" (brightness) plus xx. It does not matter if the dye is already present; only the increase in the signal (above the earlier recorded "background") is needed threshold triggering. (See Comments below for an alternative to threshold—triggering.)

Inject 3–4 ml (or an appropriate dose) of fluorescein through intravenous tap.

On the earliest appearance of the fluorescein in the field of view (FoV—i.e. the focal plane), and at an image brightness equal to or greater than the threshold, the evolving filling of the vessels in the FoV is captured and stored in the computer memory. Only a few (consecutive) frames (<10), when the fluorescein signal begins to appear and increase (in the vessels) are useful. The brightening spots in these few frames suggest the location(s) of the feeder vessels because (they are filled first). The rest of each of these few frames should remain darker (as they are yet to be filled at this time). The fluorescein filling begins in the choroid (below the retina). However, the Retinal Pigment Epithelium (RPE—the pigmented layer between the choroid and the retina) blocks (or strongly and significantly attenuates) the excitation illumination from reaching the choroid. The RPE also blocks the fluorescein fluorescence (if any) from the choroid. The feeders breach the RPE to feed the associated membranes in the sub-retina. These feeders (followed by the membranes) will fill after choroid filling but before the retinal vessels flash. The time lapse between choroidal and retinal filling is (usually) less than 100 milliseconds. Hence, expect a darkened image, then a sudden bright flash (as retina vessels fill). (In contrast, the eye blink response is estimated to be about 250 ms.)

If the triggering sequence is correctly captured, either of the following is expected:

spots or lines indicating where the feeders fill, followed by a spreading (fanning) out of the filling into patches in the immediate neighbourhood of the spots or lines (feeder vessels), or, spots and lines fill, followed by a spreading out of the filling, centred about the spots and lines, until the spots and lines disappear in the brightening patches.

Thus, the first few consecutive frames capture the locations of the first filling of the spots and lines that are the suspected feeders. After that, the capillaries-membranes fill—overwhelming the feeder locations or not—then the retinal vasculature begins to fill and the entire image is overwhelmed by a bright flash.

The captured sequence is displayed for the operator to inspect in order to locate the suspected feeder(s)—the spots and lines.

These first few (<10) frames are (image-processed to increase image clarity, if needed, and) stored in permanent memory (hard disk). The entire captured sequence can also be saved, as required; e.g. for demonstration purposes.

Repeat the injection and image-capture sequence, if the previous sequence is unsatisfactory. Use another 2–3 ml of fluorescein. Note that the already present fluorescein will contribute to the higher background "noise".

ICG SEQUENCE—After completing S1 and S2

Revert to "general illumination" and adjust the intensity, the focus and the magnification on the suspect area(s)—those determined by fluorescein early filling.

Change to the ICG filter set; change the illumination to infra-red (IR: (=780–790 nm); barrier ((=810–880 nm)

Adjust the IR illumination intensity—usually low; depends on the optics, the media and the amount of ICG to be injected.

ICG early filling is unlike the patchy fluorescein filling. Captured images have higher contrast, showing the sequential filling from the choroidal to the (arterial) inflow, to the fine filling of the capillaries-membranes and to the (venous) outflow of the feeders, and lastly, to the retinal vasculature. This allows for a 2-dimensional or a 3-dimensional reconstruction of the sequentially captured images to visualise the structure—direction of vessel growth, etc—of the feeders and the capillaries-membranes.

Variation A

Run the software (as before for fluorescein).

Capture an ICG early filling sequence for comparison to the fluorescein sequence to confirm the locationt) of the feeders.

Inject 2–3 ml of ICG (through the intravenous tap).

Capture the ICG early filling (as before for fluorescein). The image is black before ICG arrival. When the ICG arrives, here will be choroidal flash, followed by the filling of the feeders, (spreading out from arterial to venous), and lastly, the retinal filling.

Store the captured sequence or frames as required (as in Fluorescein Sequence).

Variation B

Select one or a few frames from the stored, early-fluorescein-filling.

Overlay the selected frame(s) on the "live" image (at the same magnification, orientation, etc). (See "self-tracking".)

Inject 2–3 ml of ICG (through the intravenous tap).

Observe the ICG filling and the staining of vessels under the superimposed (fluorescein frame).

Variation C

Inject 2–3 ml of ICG (through the intravenous tap).

Observe and directly capture (no need to use the trigger-capture) the inflow and the outflow of ICG through the (particular area of the) circulation—the filling from the arterial to the venous sides of the feeder and the membranes. Can It is possible to see where and how the ICG bolus moves through the circulation—thereby locating the feeder (arterial) input into the membrane.

The ICG fills the vessels, then is removed from the circulation. However, the ICG stains the diseased vessels (feeders) so that as time elapses, only the ICG-stained feeders will remain visible. Therefore, by adjusting the illumination intensity accordingly, the non-pathological circulation will fade out of view (in about 3–5 minutes post-injection).

Feeder locations are thus confirmed.

Maintain the same filter set, adjusting IR illumination as needed.

TREATMENT SEQUENCE—After completing S1, S2 and S3

Move the treatment laser aiming beam ((=633 nm) to the location of the feeder(s)—the ICG-stained spots (usually arterial first, if they can be differentiated).

Adjust the treatment power and the pulse duration. (Magnitudes are empirically established or estimated.) Usually, start at a lower power-duration combination, then increase until the required effect is seen on the live image. (Usually no more than 1000 mW for up to 300 ms per pulse is used.) Alternatively, fix the power-duration combination but repeat the pulsing until the required effect is seen. (The number of pulses is not fixed.)

A small amount (1–2 ml) of ICG can be simultaneously injected (to increase the signal and the laser absorption).

Fire the treatment laser on the targeted feeder (until the required effect is seen, if possible). The treatment ((=810 nm) laser delivers thermal (IR) energy to the target. It literally burns the feeders. Hence, it is important that the treatment spot be very concentrated (<(100(m) to deliver a high concentration of thermal energy and to ensure that collateral damage—damage to the neighbouring areas about and beyond the laser spot—is minimised, i.e. only the feeder is burned.

Inject a small amount (1–2 ml) of ICG to look for immediate confirmation of the treatment effect. If the treatment is effective, the feeder is blocked and the membrane does not fill (with ICG).

Depending on the FoV, the sequence may be repeated at other areas. (See "self-tracking".)

PHOTO-DYNAMIC THERAPY

A sequence similar in procedure to Photo-Dynamic Therapy (PDT) can be inserted at the end of the Treatment Sequence.

PDT uses the photo-chemical effect of a photo-sensitizer chemical which concentrates or is selectively absorbed in the pathological neo-vascular vessels. The photo-sensitizer does not stain or only minimally concentrates in healthy areas. The stained pathological areas are exposed to the sensitizer's waveband at low intensities for extended periods. On activation (by the illumination), the photo-sensitizer releases singlet oxygen and/or other highly reactive intermediates ("free radicals") which can cause cellular damage in (the cell membranes of) the pathological new-growth vessels, which may result in thrombosis of the vessels. It has been found that PDT may be more efficaciously applied on capillaries (in the membranes) than on the feeders (nourishing the membranes). It has been observed that the capillaries regrow within 12 weeks of the last PDT treatment. (U Schmidt-Erfurth, ARCHIVE of OPHTHALMOLOGY, 117#9, 1177–1187, September 1999.) I broke into a new paragraph.

ICG can be analogously considered as such a photo-sensitizer in our application. The principal difference is that ICG does not release "free radicals" or such. It operates with low a purely thermal effect. Like PDT, the ICG is similarly exposed to power irradiation (<50 mW, for example). The value is not exactly known (depending on the staining, the optics and the ocular media).

The ICG excitation IR illumination is close to or can be the same as the treatment laser wavelength (or waveband) (This is because the overlap of ICG excitation and ICG fluorescence wavebands is relatively large. Each waveband, by itself, spans more than 100 nm.) The difference between illumination and treatment beams is that the continuous illumination is at much lower power and/or is much more diffused; while the treatment beam is much more focused (<(100(m treatment beam spot) and at much higher pulsed powers (up to 2000 mW ).

ICG stains the capillaries in the membrane as well as the larger feeder-vessels. At low IR power, the feeders themselves cannot be photocoagulated. (Only the above-mentioned ICG and Treatment Sequences can destroy the larger feeders). However, it may be possible to destroy the membrane capillaries using this long, low-power exposure on ICG. As such, the entire ICG and Treatment Sequences is, in effect, a PDT Sequence as well (even if the PDT Sequence detailed below is not used as part of the viewing and treatment procedure outline in the flowchart above). This is because the continuous, diffused, low-power, ICG-excitation, IR illumination is always present in the ICG and the Treatment sequences. Hence, depending on the duration of the ICG and the Treatment Sequences, the capillaries-membranes are in effect being treated as well. (The ICC and the Treatment Sequences are meant to locate and destroy the feeders only. Note that the feeder signals may be harder to extract in the presence of nearby or overlying membranes.)

If this is indeed the case, the patient may leave after this low-power exposure, i.e. the sequence may be interrupted. After 1 to 2 weeks, the patient should be recalled for all the above sequences. If the PDT Sequence is successful, the capillaries, and therefore the membrane, do not accept (fluorescein and) ICG: they do not fill and no signal is emitted. However, the larger undamaged feeders will remain and will be stained and be fluorescent. The advantage of this is that the background noise is reduced (as the once-surrounding or overlying membrane does not fluoresce). The feeders are then more easily, more exactly located and more distinctly seen so that the Treatment Sequence can be more precisely applied.

In this manner, the capillaries-membranes are first destroyed as part of the procedure for locating the feeders. Then, the feeders are targeted and destroyed in the follow-up.

PDT SEQUENCE—After completing S1, S2, S3 and maybe, S4

Revert to "general illumination" and adjust the intensity, the focus and the magnification on suspect area(s)—those determined by fluorescein early filling images, or, broad areas without specific targets.

Change (or maintain) the filter set for ICG and infra-red illumination (IR: (=780–790 nm).

Adjust the IR intensity slightly higher than before (but <50 mW), depending on the optics, the media and the amount to ICG to be injected.

Inject (up to 10 ml) of ICG, if needed, (determined by patient's body weight).

Expose the suspect area to IR for extended periods (>15 minutes). The exact exposure duration is unknown.

Variation A

The PDT Sequence can be carried out after executing the ICG and the Treatment Sequences because the diseased capillaries-membrane are not treated—too small or too fine, over too wide areas for the Treatment Sequence to be applied. Hence, apply the PDT Sequence after the feeder treatment to destroy the remaining capillaries-membranes.

Variation B

The PDT Sequence can be carried out before executing the Treatment Sequence, especially if the feeders cannot be clearly located because they are hidden by the overlying capillaries-membranes. In this case, apply the PDT Sequence to destroy the capillaries-membranes to reduce their "noise" contribution to the image so that the underlying feeders can be more clearly defined by a re-execution of the Fluorescein and the ICG Sequences (which may be carried out 1 or 2 weeks after the PDT Sequence).

EXAMPLE 2

Using Extensive RAM

Example 1 is repeated using very large (image) storage memory as an alternative to threshold triggering. Upon injection of any dye, the system immediately begins to capture and store all incoming images (at 60 frames per second or faster). With ample memory which provides the needed extended period of image capturing, the early filling is captured within 10–15s from injection. This takes care of false triggering due to over-sensitive threshold, or, no (or late) triggering due to overly high threshold setting (i.e. xx set too large). This setup has the added advantage of capturing any "anomalous" events before or after the first visual appearance of the dye. Note that the fast electronic sensor (CCD camera) can detect "brightness" increases that are still invisible to the human eye, or, that can be displayed (without enhancement) on the monitor screen. The user will, however, have to select those frames to be saved (on hard disk) as saving the entire captured sequences will require too much memory (on the hard disk) and will also take too long to complete.

The invention thus provides methods for identifying and treating neovascularization such as in AMD.

What is claimed is:

1. A method of treating a neovascularization in the eye of a patient, comprising:

permitting a photosensitizer chemical to enter the neovascularization;

photocoagulating a feeder vessel to substantially prevent said vessel from feeding blood to the neovascularization; and after photocoagulating the feeder vessel, activating the photosensitizer chemical to destroy the neovascularization.

2. A method of treating a neovascularization in the eye of a patient comprising:

introducing a photosensitizer chemical into the circulation of the patient at a point remote from the eye, wherein said photosensitizer chemical is activated upon exposure to radiation having a wavelength within an absorption waveband of said photosensitizer chemical;

locating a feeder vessel through which blood flows to the region of neovascularization;

permitting the photosensitizer chemical to enter the neovascularization;

photocoagulating the feeder vessel to substantially prevent said vessel from feeding blood to the neovascularization thereby providing a substantially reduced blood flow within the neovascularization; and after photocoagulating the feeder vessel, activating the photosensitizer chemical by exposure to said radiation to produce either a photochemical effect or a photothermal effect or both a photochemical effect and a photothermal effect within the reduced blood flow of the neovascularization which in effect destroys the neovascularization.

3. A method according to claim 2, wherein no significant photochemical or photothermal effect occurs in blood vessels which do not have a substantially reduced blood flow caused by photocoagulation thereof, thereby ensuring that blood vessels and tissues unrelated to the neovascularization remain substantially undamaged during the treatment process.

4. A method according to claim 2, wherein the photosensitizer chemical is activated by a level of radiation which is effective to induce either the photothermal effect or the photochemical effect or both the phothermal effect and the photochemical effect within the reduced blood flow of the neovascularization, and wherein the level of radiation causes substantially no damage to blood vessels or tissues unrelated to the neovascularization.

5. A method according to claim 2, wherein the photosensitizer chemical is activated by a diffused and/or low level of radiation.

6. A method according to claim 2, wherein the photosensitizer chemical is employed in combination with a detectable marker, which detectable marker is different from the photosensitizer chemical and is employed to locate the feeder vessel by detecting the location of the onset of the marker into the region of neovascularization.

7. A method according to claim 6, wherein the photosensitizer chemical is indocyanine green (ICG) and the detectable marker is fluorescein.

8. A method according to claim 2, wherein the photosensitizer chemical is also a detectable marker.

9. A method according to claim 8, wherein the photosensitizer chemical is employed to locate the feeder vessel by detecting the location of the onset of the marker into the region of neovascularization.

10. A method according to claim 8, wherein the photosensitizer chemical is employed to determine the positions of blood vessel walls in the region of neovascularization.

11. A method according to claim 8, wherein the photosensitizer chemical is indocyanine green (ICG).

12. A method according to claim 2, comprising:
introducing a detectable marker into the circulation of the patient at a point remote from the eye;
observing a region of suspected neovascularization in the eye after introducing the marker; and
detecting the location of the onset of the marker into the region in order to determine the location of a feeder vessel to the region of neovascularization or an anomaly in the retinal pigment epithelium.

13. A method according to claim 12, wherein photocoagulation of the feeder vessel is achieved without substantial damage to blood vessels or tissues unrelated to the neovascularization.

14. A method according to claim 12, wherein the marker is a fluorescent dye, the region is illuminated by radiation that excites the dye and the first appearance of the dye in the region is detected as an increase in brightness by a predetermined amount above background levels.

15. A method according to claim 12, wherein the feeder vessel is treated by using a laser.

16. A method according to claim 15, comprising treating the feeder vessel using a laser wherein the waveband of the laser is the same as the absorption peak in the waveband of the second detectable marker.

17. A method according to claim 12, wherein a change in brightness is measured at the location of the onset of the marker and recorded against time to facilitate determining the location of the earliest onset of the marker into the feeder vessel.

18. A method according to claim 17, wherein the change in brightness is recorded graphically.

19. A method according to claim 12, further comprising introducing a second detectable marker into the circulation of the patient, and detecting the location of the second detectable marker in the region so as to determine the positions of blood vessel walls in the region.

20. A method according to claim 19, comprising comparing the location of the first appearance of the first detectable marker into the region with the position of the blood vessel walls located by the second detectable marker to determine and/or confirm the location of a feeder vessel feeding blood into the region.

21. A method according to claim 19, wherein an image or images showing the earliest appearance of the first marker is made semi-transparent and then is superimposed on the real-time image in which the second marker is introduced, the presence of the second marker in underlying locations in real-time indicating the suspected feeder vessel; and absence of the second marker in underlying locations indicating that the suspected feeder vessel has been coagulated successfully.

22. A method according to claim 12, wherein the region is observed by recording a succession of images of the region using an image recorder and subsequently examining the recorded images to identify the location of a feeder vessel feeding blood into the region.

23. A method according to claim 22, wherein the image recorder captures images at a rate of at least 30 per second.

24. A method according to claim 22, wherein recording of images of the region is triggered by trigger means associated with the image recorder and sensitive to an increase of the marker in the region.

25. A method for treating neovascularization according to claim 12, in a Choroidal Neo-Vascular Membrane (CNVM) in Age-related Macular Degeneration (AMD).

26. A method according to claim 25, wherein the AMD is an exudative form of Age-related Macular Degeneration.

27. A method according to claim 25, wherein blood supply to the neovascularization in the CNVM is substantially ceased by photocoagulation of a few feeder vessels feeding blood into the neovascularization.

28. A method according to claim 27, wherein one to three feeder vessels are photocoagulated.

* * * * *